United States Patent
Zhang et al.

(10) Patent No.: US 10,012,744 B2
(45) Date of Patent: Jul. 3, 2018

(54) IMAGING DEVICE USING A CLOSE PROXIMITY TAG TO CONFIGURE A WIRELESS LOCAL AREA NETWORK (LAN) TRANSCEIVER

(71) Applicant: VAREX IMAGING CORPORATION, Salt Lake City, UT (US)

(72) Inventors: Yao Zhang, Salt Lake City, UT (US); Mark D Batts, Sandy, UT (US); Keith Douglas Gray, San Ramon, CA (US)

(73) Assignee: VAREX IMAGING CORPORATION, Salt Lake City, UT (US)

( * ) Notice: Subject to any disclaimer, the term of this patent is extended or adjusted under 35 U.S.C. 154(b) by 0 days.

(21) Appl. No.: 15/018,362

(22) Filed: Feb. 8, 2016

(65) Prior Publication Data

US 2017/0227660 A1    Aug. 10, 2017

(51) Int. Cl.

| | |
|---|---|
| *G01T 7/00* | (2006.01) |
| *H04W 76/11* | (2018.01) |
| *H04W 4/80* | (2018.01) |
| *A61B 6/00* | (2006.01) |
| *G01T 1/17* | (2006.01) |
| *G01T 1/20* | (2006.01) |
| *H04W 4/00* | (2018.01) |
| *H04W 76/02* | (2009.01) |
| *H04W 12/04* | (2009.01) |

(Continued)

(52) U.S. Cl.
CPC ............... *G01T 7/00* (2013.01); *A61B 6/563* (2013.01); *G01T 1/17* (2013.01); *G01T 1/20* (2013.01); *H04W 4/008* (2013.01); *H04W 4/80* (2018.02); *H04W 12/04* (2013.01); *H04W 76/021* (2013.01); *H04W 76/11* (2018.02); *H04W 24/02* (2013.01); *H04W 84/12* (2013.01)

(58) Field of Classification Search
None
See application file for complete search history.

(56) References Cited

U.S. PATENT DOCUMENTS

| | | | | |
|---|---|---|---|---|
| 8,381,270 | B1 * | 2/2013 | Hsieh ................. | H04L 41/0806 726/4 |
| 2012/0057673 | A1 * | 3/2012 | Campbell ............. | G01N 23/04 378/62 |

OTHER PUBLICATIONS

Chandler, Nathan "What's an NFC tag?" webpage <http://electronics.howstuffworks.com/nfc-tag.htm>, accessed Feb. 5, 2016, published on Mar. 14, 2012, HowStuffWorks.com.

(Continued)

*Primary Examiner* — Edwin Gunberg
(74) *Attorney, Agent, or Firm* — Su IP Consulting

(57) ABSTRACT

Technology is described for imaging device (e.g., x-ray detector) that includes a tag reader. In one example, the imaging device includes a imaging matrix of pixel detector elements, a wireless local area network (LAN) transceiver, a tag reader, and a controller. Each pixel detector element is configured to detect photon energy. The wireless LAN transceiver is configured to transmit imaging matrix data to at least one wireless access point (WAP). The tag reader is configured to read WAP configuration data from a close proximity tag. The controller is coupled to the imaging matrix, the wireless LAN transceiver, and the tag reader. The controller is configured to initialize the wireless LAN transceiver for communication with a specified WAP using the WAP configuration data. The at least one WAP includes the specified WAP.

18 Claims, 13 Drawing Sheets

(51) Int. Cl.
*H04W 84/12* (2009.01)
*H04W 24/02* (2009.01)

(56) References Cited

OTHER PUBLICATIONS

Pinola, Melanie "What Is NFC and How Can I Use It?," webpage http://lifehacker.com/5943006/what-is-nfc-and-how-can-i-use-it, accessed Feb. 5, 2016, published on Sep. 13, 2012.
IHaveAnEvo1 "How to Set Up NFC Tags," multimedia webpage https://www.youtube.com/watch?v=ZUFMLpJUT70, accessed Feb. 5, 2016, published on Jun. 14, 2013.

* cited by examiner

US 10,012,744 B2

IMAGING DEVICE USING A CLOSE PROXIMITY TAG TO CONFIGURE A WIRELESS LOCAL AREA NETWORK (LAN) TRANSCEIVER

BACKGROUND

Unless otherwise indicated herein, the approaches described in this section are not prior art to the claims in this disclosure and are not admitted to be prior art by inclusion in this section.

An x-ray system typically includes an x-ray tube and a detector. The power and signals for the x-ray tube can be provided by a tube generator. The x-ray tube emits radiation, such as x-rays, toward an object. The object is positioned between the x-ray tube and the detector. The radiation typically passes through the object and impinges on the detector. As radiation passes through the object, internal structures of the object cause spatial variances in the radiation received at the detector. The detector then generates data based on the detected radiation, and the system translates the radiation variances into an image, which may be used to evaluate the internal structure of the object, such as a patient in a medical imaging procedure or an inanimate object in an inspection scan.

The radiation detector (e.g., x-ray detector) can include a conversion element that converts an incoming radiation beam into electrical signals, which can be used to generate data about the radiation beam, which in turn can be used to characterize an object being inspected (e.g., the patient or inanimate object). In one example, the conversion element includes a scintillator that converts a radiation beam into light, and a sensor that generates electrical signals in response to the light. The detector can also include processing circuitry that processes the electrical signals to generate data about the radiation beam.

In some configurations, the radiation detector can be portable to allow images to be taken of the object in different positions or at different angles. The portable radiation detector can communicate with the rest of the imaging system, which can include the radiation source (e.g., x-ray tube) and image signal generator, via a wired or optical link (e.g., cable) or a wireless link (e.g., WiFi transceiver). The radiation detector may also be used or shared by various radiation sources (e.g., x-ray tube) or workstations (e.g., computer) in various locations (e.g., rooms). As such, the radiation detector may be reconfigured each time the detector is used with a different radiation source, workstation, or location. The technology (devices, systems, and methods) described herein provides solutions to configure an imaging device (e.g., radiation detector) to a workstation or a radiation source.

BRIEF SUMMARY OF SOME EXAMPLE EMBODIMENTS

An imaging device (e.g., radiation detector) can be directly coupled via a cable to a workstation used to control an imaging system, process image data, or store image data. Using a cable can be problematic. For example, the length of the cable can limit the range or the position that the imaging device can be used, the cable can get lost or misplaced, the cable can cause a tripping hazard, or the cable or cable connectors can wear out or become damaged. An imaging device that includes a wireless transceiver (e.g., a wireless local area network [LAN] transceiver) can also communicate with the workstation coupled to a wireless access point (WAP) using a wireless protocol (e.g., WiFi), which can reduce the use of a cable. A service cable (or network cable) may still be needed to initially configure the wireless transceiver to communicate with the workstation, and the remaining data communication can occur between the wireless LAN transceiver and the WAP. The service cable may be eliminated entirely for configuring the wireless transceiver by using a close proximity tag.

In an example, the imaging device includes an imaging matrix of pixel detector elements, a wireless LAN transceiver, a tag reader, and a controller. Each pixel detector element is configured to detect photon energy. The wireless LAN transceiver is configured to transmit imaging matrix data to at least one WAP. The tag reader is configured to read WAP configuration data from a close proximity tag (i.e., a first close proximity tag). The controller is coupled to the imaging matrix, the wireless LAN transceiver, and the tag reader. The controller is configured to initialize the wireless LAN transceiver for communication with a specified WAP using the WAP configuration data. The at least one WAP includes the specified WAP.

For example, the tag reader can include a near field communication (NFC) reader, a radio-frequency identification (RFID) reader, an optical reader, and a barcode reader, and the close proximity tag can include a NFC tag, a RFID microchip, a scannable image, or a barcode. The WAP configuration data can include a service set identifier (SSID), an Internet Protocol address (IP address), a passphrase, a country code, or a channel. The wireless LAN transceiver is configured to communicate using a WiFi, Institute of Electrical and Electronics Engineers (IEEE) 802.11 standard, Bluetooth, or IEEE 802.15 wireless communication standard.

In another example, the tag reader is configured to read a control function code from the close proximity tag or a second close proximity tag. The control function code can include an image device setting or a reset to default settings command. In a configuration, the imaging device is an radiation detector, the imaging matrix is an radiation imaging matrix, and each pixel detector element is an radiation pixel detector element configured to detect radiation. The radiation imaging matrix can include a scintillator layer.

In another configuration, the imaging device includes an energy storage component, such as a battery or a capacitor, configured to provide power to the imaging device. The imaging device can also include an indicator configured to provide an indication that the specified WAP is configured for communication with the imaging device. The indicator can include a speaker, a light, a light emitting diode (LED), or a display. In another example, the imaging device includes a motion sensor configured to detect motion of the imaging device and the detected motion is used to wake up at least a portion of circuitry of the imaging device. The motion sensor can include a motion detector, an accelerometer, a gyrometer, a gyroscope, or a rotation sensor.

Another example provides a method of configuring an imaging device for communication with a WAP using a close proximity tag. The method includes the operation of retrieving WAP configuration data from a close proximity tag (i.e., a first close proximity tag) by a tag reader on an imaging device. The tag reader on the imaging device is placed with a detectable range (e.g., within one meter) of the close proximity tag. The next operation of the method can include configuring a wireless LAN transceiver to communicate with a WAP associated with the WAP configuration data.

In another example, the method can further include communicating with the WAP via the wireless LAN transceiver. The communication includes transmission of image data from the imaging device. The imaging device can be a radiation detector that is configured to detect radiation and the image data can include an image generated from x-rays. The communication with the WAP via the wireless LAN transceiver can use at least one wireless communication standard, such as WiFi, IEEE 802.11 standard, Bluetooth, and IEEE 802.15 standard. The WAP configuration data includes a SSID, an IP address, a passphrase, a country code, or a channel.

The tag reader can include a near field communication (NFC) reader, a radio-frequency identification (RFID) reader, an optical reader, and a barcode reader, and the close proximity tag can include a NFC tag, a RFID microchip, a scannable image, or a barcode. In another example, the method can further include generating an indication when the wireless LAN transceiver is configured to communicate with the WAP. The indicator can include a speaker, a light, a LED, or a display.

In another example, the method can further include retrieving embedded control function code from the second close proximity tag by the tag reader on the imaging device. The tag reader on the imaging device is placed within a detectable range of the second close proximity tag. The method can further include performing a control function on the imaging device based on the embedded control function code, such as an imagge device setting or a reset to default settings command.

In another example, the method can further include programming the close proximity tag with the WAP configuration data using a tag programmer. The tag programmer is placed within a detectable range of the close proximity tag. The next operation of the method can include positioning the close proximity tag within a communication range of the WAP.

In an example, a radiation detector includes a radiation imaging matrix of radiation pixel detector elements, a WiFi transceiver, an NFC reader, and a controller. Each radiation pixel detector element is configured to detect radiation. The WiFi transceiver is configured to transmit radiation imaging matrix data to at least one WAP. The NFC reader is configured to read WAP configuration data from a NFC tag. The controller is coupled to the radiation imaging matrix, the WiFi transceiver, and the NFC reader, and the controller is configured to initialize the WiFi transceiver for communication with a specified WAP using the WAP configuration data. The at least one WAP includes the specified WAP.

The summary provided above is illustrative and is not intended to be in any way limiting. In addition to the examples described above, further aspects, features, and advantages of the invention will be made apparent by reference to the drawings, the following detailed description, and the appended claims.

DETAILED DESCRIPTION OF SOME EXAMPLE EMBODIMENTS

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Numbers provided in flow charts and processes are provided for clarity in illustrating steps and operations and do not necessarily indicate a particular order or sequence. Unless otherwise defined, the term "or" can refer to a choice of alternatives (e.g., a disjunction operator, or an exclusive or) or a combination of the alternatives (e.g., a conjunction operator, and/or, a logical or, or a Boolean OR).

Disclosed embodiments relate generally to an imaging device that includes a wireless LAN (e.g., WiFi) transceiver and a tag reader (e.g., NFC reader) and methods for configuring the wireless LAN transceiver and the imaging device using close proximity tags and the tag reader. Example embodiments illustrate mechanisms and methods to configure the wireless LAN transceiver and the imaging device without using a service cable.

Reference will now be made to the drawings to describe various aspects of example embodiments of the invention. It is to be understood that the drawings are diagrammatic and schematic representations of such example embodiments, and are not limiting of the present invention, nor are they necessarily drawn to scale.

Figure 1:
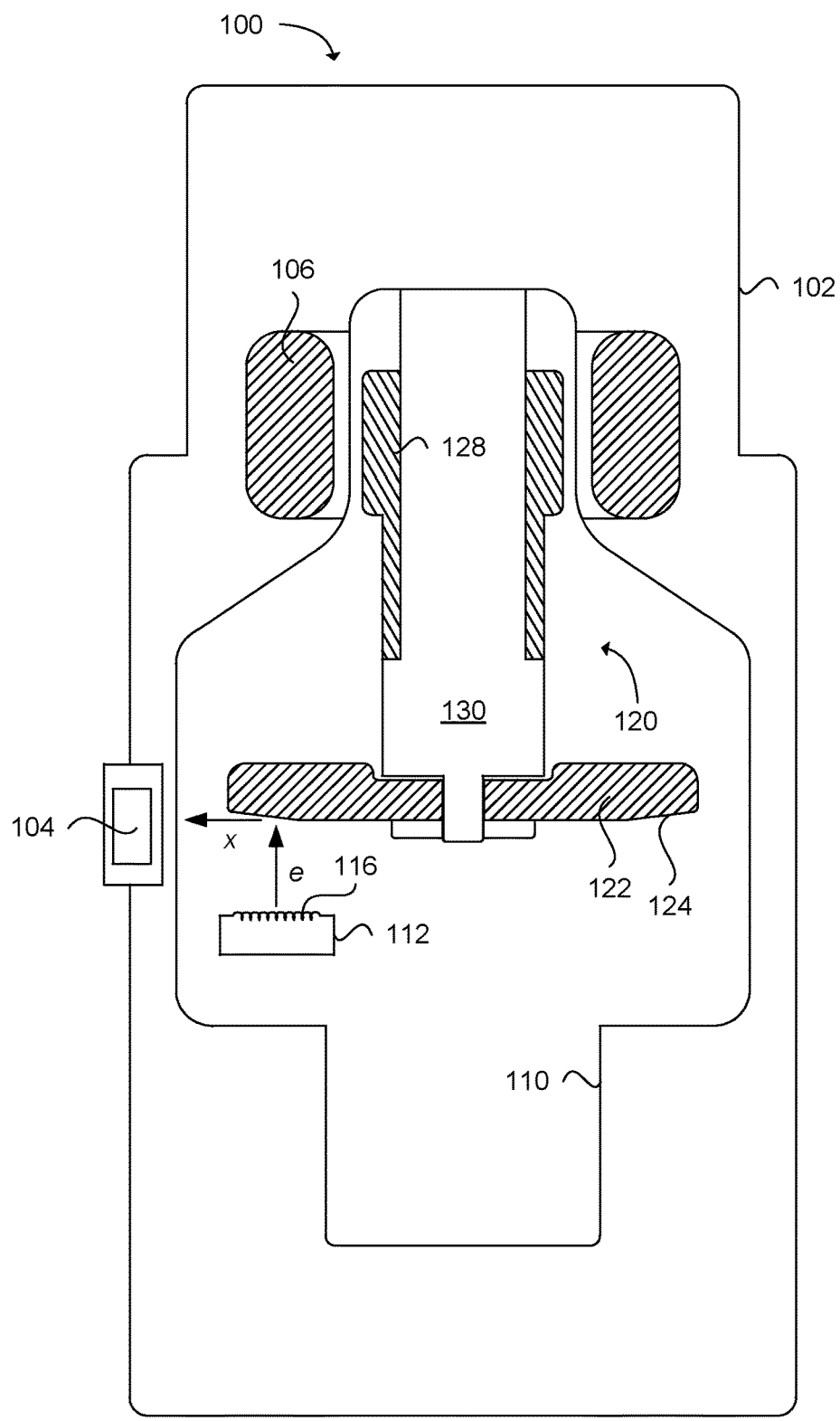
FIG. 1 illustrates a block diagram of an example x-ray tube.

FIG. 1 is a block diagram of an example rotary or rotating anode type x-ray tube 100 with a rotatable disc-shaped anode 122. The x-ray tube 100 includes a housing 102 and an x-ray insert 110 within the housing 102. The housing 102 encloses the insert 110. A coolant or air may fill the space or cavity between the housing 102 and the insert 110. A cathode 112 and an anode assembly 120 are positioned within an evacuated enclosure, also referred to as the insert 110. The anode assembly 120 includes the anode 122, a bearing assembly 130, and a rotor 128 mechanically coupled to the bearing assembly 130. The anode 122 is spaced apart from and oppositely disposed to the cathode 112. The anode 122 and cathode 112 are connected in an electrical circuit that allows for the application of a high voltage potential between the anode 122 and the cathode 112. The cathode 112 includes an electron emitter 116 that is connected to an appropriate power source (not shown).

As disclosed in FIG. 1, prior to operation of the example x-ray tube 100, the insert 110 is evacuated to create a vacuum. The insert 110 encloses the vacuum. Then, during operation of the example x-ray tube 100, an electrical current is passed through the electron emitter 116 of the cathode 112 to cause electrons "e" to be emitted from the cathode 112 by thermionic emission. The application of a high voltage differential between the anode 122 and the cathode 112 then causes the electrons "e" to accelerate from the cathode electron emitter toward a focal spot on a focal track 124 that is positioned on the anode 122. The focal track 124 may be composed for example of tungsten (W) and rhenium (Re) or other materials having a high atomic ("high Z") number. As the electrons "e" accelerate, they gain a substantial amount of kinetic energy, and upon striking the rotating focal track 124 some of this kinetic energy is converted into x-rays "x".

The focal track 124 is oriented so that emitted x-rays "x" are visible to an x-ray tube window 104. The x-ray tube window 104 includes an x-ray transmissive material, such as beryllium (Be), so the x-rays "x" emitted from the focal track 124 pass through the x-ray tube window 104 in order to strike an intended object (not shown) and then the detector to produce an x-ray image (not shown). FIG. 1 illustrates a single window 104 on the housing 102 (e.g., with a glass insert that allows radiation to pass through the glass of the insert). In other examples, a separate window may be included on both the insert 110 (e.g., a metal insert) and the housing 102, or a window may be included on just the insert 110.

As the electrons "e" strike the focal track 124, a significant amount of the kinetic energy of the electrons "e" is transferred to the focal track 124 as heat. To reduce the heat at a specific focal spot on the focal track 124, a disc-shaped anode target is rotated at high speeds, typically using an induction motor that includes a rotor 128 and a stator 106. The induction motor is an alternating current (AC) electric motor in which the electric current in the rotor 128 needed to produce torque is obtained by electromagnetic induction from a magnetic field of stator winding. Then, the rotor 128 rotates a hub of the bearing assembly 130 that is mechanically coupled to the anode 122, which rotates the anode 122. In other examples (not shown), the x-ray tube uses a stationary track.

Figure 2:
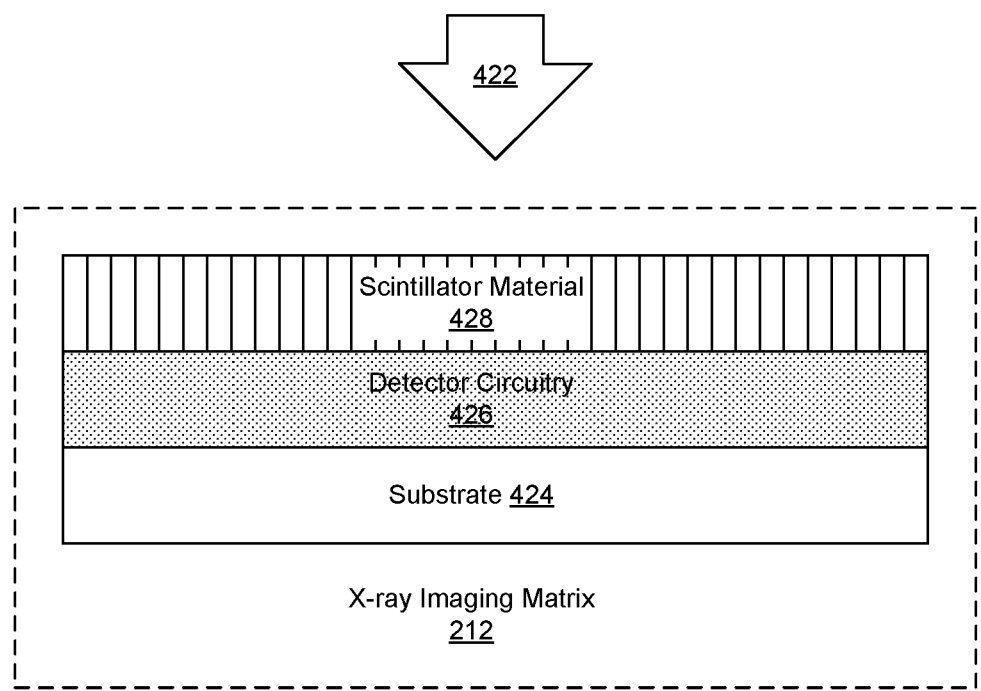
FIG. 2 illustrates a side view of layers in an example x-ray detector element of and x-ray imaging matrix in an x-ray detector.

After the x-rays are emitted from the x-ray tube, the x-rays strike an intended object (e.g., the patent or inanimate object) and then the radiation detector to produce an x-ray image. The radiation detector includes a matrix or array of pixel detector elements. The pixel detector elements (e.g., x-ray detector element or detector element) refer to an element in a matrix or array that converts x-ray photons to electrical charges. A detector element may include a photoconductor material which can convert x-ray photons directly to electrical charges (electron-hole pairs) in a direct detection scheme. Suitable photoconductor material include and are not limited to mercuric iodide ($HgI_2$), lead iodide ($PbI_2$), bismuth iodide ($BiI_3$), cadmium zinc telluride (CdZnTe), or amorphous selenium (a-Se). In some embodiments, a detector element may comprise a scintillator material which converts x-ray photons to light and a photosensitive element coupled to the scintillator material to convert the light to electrical charges (i.e., indirect detection scheme), as illustrated in FIG. 2. FIG. 2 illustrates a radiation source 422 relative to the layers of an x-ray imaging matrix 212 using the indirect detection scheme, which includes a substrate 424, photosensitive element and detector circuitry 426, and a layer of scintillator material 428. The x-ray imaging matrix 212 may include other layers, sections shown may include multiple layers (e.g., detector circuitry 426 includes multiple processing layers), or the layers may be in a different order. Suitable scintillator materials include and are not limited to gadolinium oxisulfide ($Gd_2O_2S$:Tb), cadmium tungstate ($CdWO_4$), bismuth germanate ($Bi_4Ge_3O_{12}$ or BGO), cesium iodide (CsI), or cesium iodide thallium (CsI:Tl)). Suitable photosensitive element may include a photodiode, a photogate, or phototransistors. Other circuitry for pixel detector elements may also be used.

The x-ray tube and radiation detector can be components in an imaging system that are located in an x-ray room. A healthcare provider (e.g., hospital) may have multiple x-ray rooms each equipped with computer workstation and an x-ray source (e.g., x-ray tube and tube generator). A radiation detector (e.g., wireless flat panel wireless portable x-ray detector) can be shared among multiple x-ray rooms by communicating with a workstation located in each x-ray room. Each x-ray source can have a workstation associated with the x-ray source and each workstation can be coupled to a wireless access point (WAP) associated with the workstation. The radiation detector can include a wireless local area network (LAN) transceiver (e.g., WiFi transceiver) that communicates with the WAP. A wireless transceiver is a device that is configured to transmit or receive wireless signals via an air interface. A LAN is a computer network that interconnects computers within a limited area such as a residence, school, laboratory, or office building. Local refers to the range of the area network. The embodiments described can also apply to other area networks, such as wide area networks (WANs) and personal area networks (PANs). The WAN is a telecommunications network or computer network that extends over a large geographical distance, and the PAN is a computer network used for data transmission among devices such as computers, telephones and personal digital assistants. As used herein, LAN refers to a LAN and smaller area networks, such as PANs. In some embodiments, LAN can refer to a LAN and larger area networks, such as a WAN. A wireless LAN (WLAN) is a wireless computer network that links two or more devices using a wireless distribution method (e.g., spread-spectrum or orthogonal frequency-division multiplexing [OFDM] radio) within the LAN. Many WLANs are based on Institute of Electrical and Electronics Engineers (IEEE) 802.11 standards (e.g., 802.11ac, 802.11ad), which is commonly known to industry groups as WiFi (Wi-Fi). A WLAN may also use another technology besides WiFi. A wireless PAN (WPAN) is a PAN carried over wireless network technologies such as Bluetooth, Wireless Universal Serial Bus (USB), or ZigBee. Bluetooth is a wireless technology standard for exchanging data over short distances (e.g., using short-wavelength ultrahigh frequency [UHF] radio waves in the industrial, scientific and medical [ISM] radio band from 2.4 to 2.485 gigahertz [GHz]). Wireless USB is a short-range, high-bandwidth wireless radio communication protocol which can increase the availability of general USB-based technologies. ZigBee is an IEEE 802.15.4-based specification for a suite of high-level communication protocols. A wireless WAN (WWAN) is a WAN carried over a wireless network using mobile telecommunication cellular network technologies such as such as the third generation partnership project (3GPP) long term evolution (LTE) (e.g., Release 11 or 12), High Speed Packet Access (HSPA), or IEEE 802.16 standard (e.g., 802.16e, 802.16m), which is commonly known to industry groups as WiMAX (Worldwide interoperability for Microwave Access). The WAP (or receptor) is a networking hardware device that allows wireless devices to connect to a wired network using a wireless protocol (e.g., WiFi). The WAP may be an external device associated with a workstation or integrated into a workstation (e.g., laptop computer).

Typically, x-ray rooms are lined with a shielding material (e.g., lead) that blocks electromagnetic radiation, such as x-radiation radiation or x-ray electromagnetic radiation, from leaving the room and exposing those outside the room unnecessarily to the radiation. X-radiation (composed of x-rays) is a form of electromagnetic radiation that has a wavelength ranging from 0.01 to 10 nanometers (nm), corresponding to frequencies in the range 30 petahertz to 30 exahertz ($3 \times 10^{16}$ Hz to $3 \times 10^{19}$ Hz) and energies in the range 100 electronvolts (eV) to 100 kiloelectronvolts (keV). The same shielding material that blocks x-rays can also block the radio frequency (RF) signals used by the wireless LAN transceivers of radiation detectors to communicate with WAPs outside the x-ray room. So, each workstation in an x-ray room may have its own WAP or a group of workstations in an x-ray room may have their own WAP. Each WAP can have a different configuration from other WAPs, which needs to be known or identified by the radiation detector (e.g., the portable radiation detector) before the radiation detector can be used with the workstation in communication with the WAP.

Figure 3:
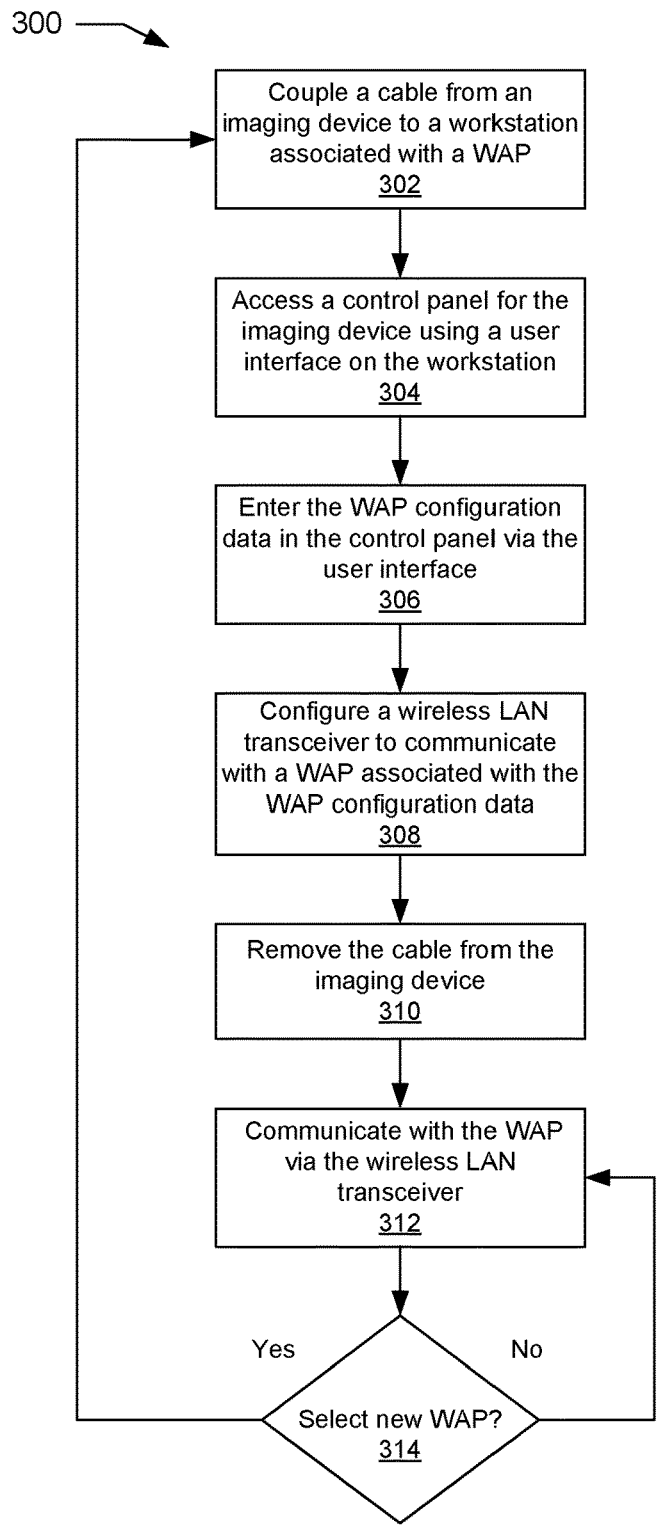
FIG. 3 illustrates a flowchart for configuring an imaging device for communication with a WAP using a service cable.

In one example, a cable (e.g., service cable or network cable) is used to physically attach a radiation detector (e.g., panel or flat panel) to the workstation and the workstation sends configuration information to the portable detector, as illustrated in the flowchart 300 shown in FIG. 3. For example, a cable can be coupled from a imaging device (e.g., radiation detector) to a workstation associated with a WAP 302. Then a user accesses a control panel (e.g., web page) for the imaging device using a user interface (e.g., graphical user interface [GUI] or web browser) on a display of the workstation 304. The user enters the WAP configuration data in the control panel via the user interface 306. Using the WAP configuration data, a wireless LAN transceiver is configured to communicate with a WAP associated with the WAP configuration data 308. The cable is removed from the imaging device 310. And the wireless LAN transceiver communicates with the WAP 312, which can include imaging data, until another WAP is selected. When or if a new WAP is selected 314, the process 300 of using the cable 302 is repeated.

The WAP configuration data can include information used to configure a wireless LAN transceiver for a specified WAP. For example, using the WiFi communication protocol, the WAP configuration data can include a service set identifier (SSID), an Internet Protocol address (IP address), a passphrase, a country code, a channel, and other similar configuration data. The SSID (e.g., SSID=VMSXWv4) differentiates one WLAN from another. Access points (WAPs) and devices attempting to connect to a specific WLAN can use the same SSID to enable effective roaming. As part of the association process, a wireless network interface card (NIC) in a device has the same SSID as the access point or device is not permitted to join a basic service set (BSS). The IP address (IPADDR=192.168.2.31/24) is a numerical label assigned to each device (e.g., computer) participating in a computer network (e.g., WLAN) that uses the Internet Protocol (IP) for communication. A passphrase is a sequence of words, text, letters, numbers, or special characters used to control access to a network, computer system, program, or data. Each wireless network device can encrypt the network traffic using a 256 bit key (e.g., passphrase). This encryption key may be entered either as a string of 64 hexadecimal digits, or as a passphrase (e.g., PASSPHRASE=abcd1234) of 8 to 63 printable American Standard Code for Information Interchange (ASCII) characters. The country code (e.g., COUNTRY=US) provides the location of the WLAN. Each of the countries applies its own regulations to the allowable channels, allowed users, and maximum power levels within these frequency ranges used by the WLAN. The country code can be used to set the allowable channels (e.g., RF frequencies), allowed users, and maximum power levels within the allowed frequency ranges. WLAN standards (e.g., WiFi) set the attributes for the different channels that may be used. The channel attributes enable different WLAN modules to talk to each other and can be used to set up a WLAN. For example, to ensure that WLAN solutions operate satisfactorily, parameters such as the RF signal center frequencies, channel numbers (e.g., CHANNEL=44), and the bandwidths are set.

As an alternative to using a cable to setup the WAP configuration data for a WLAN transceiver in an imaging device (e.g., radiation detector), a close proximity tag (e.g., NFC tag) may be used. The WAP configuration data can be embedded in the close proximity tag. The WAP configuration data on the close proximity tag can then be read by a tag reader (e.g., NFC reader) located on the imaging device, which is used to configure the WLAN transceiver.

Figure 4:
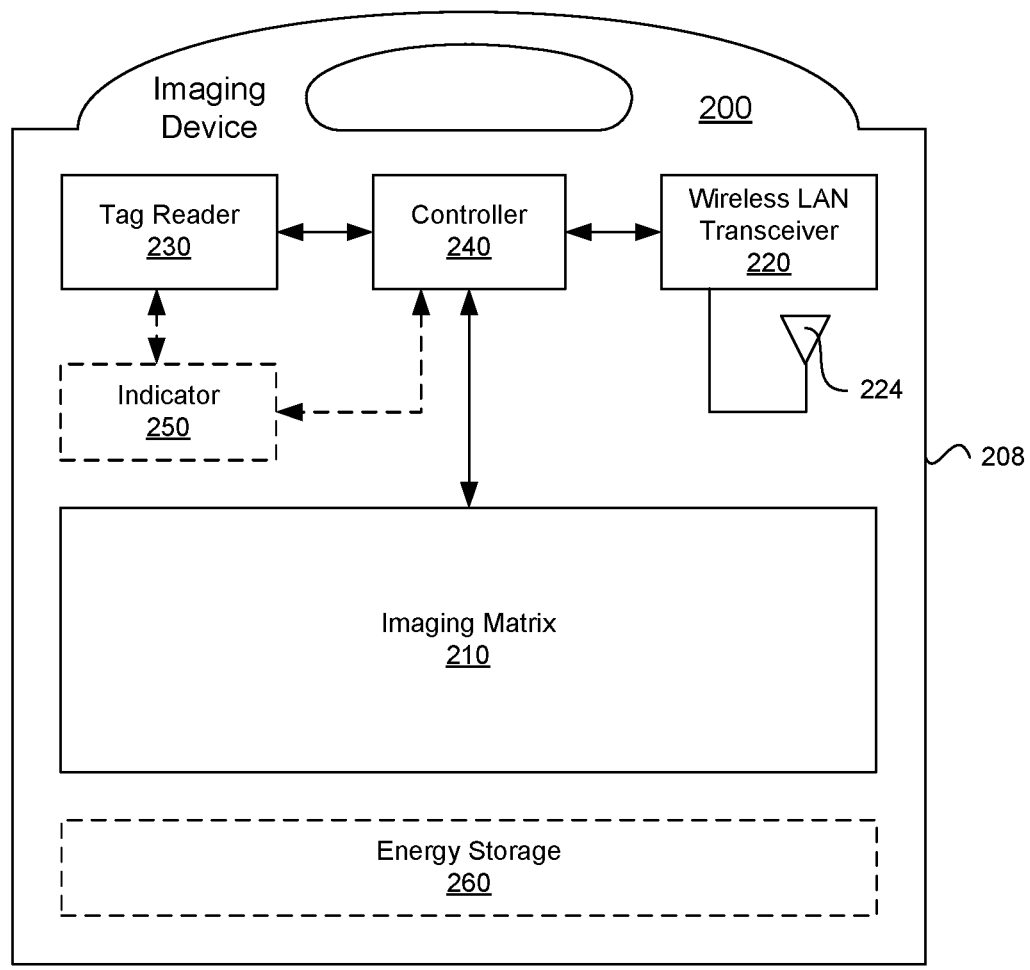
FIG. 4 illustrates a block diagram of an example imaging device with a tag reader.

FIG. 4 illustrates an imaging device 200 that includes a housing 208, an imaging matrix 210 of pixel detector elements, a wireless LAN transceiver 220 that allows wireless communication with a WAP, a tag reader 230 that reads a close proximity tag, and a controller 240 that controls the imaging device or coordinates communication between imaging device modules (e.g., wireless LAN transceiver and tag reader). In a configuration, the LAN transceiver includes multiple transceivers for different communication protocols (e.g., WPAN transceiver for Bluetooth and WLAN transceiver for WiFi). The wireless LAN transceiver 220 can include a single antenna or multiple antennas 224.

The tag reader 230 is configured to read or capture information on a close proximity tag when the tag reader is within a close distance, a detectable range, or close proximity to the close proximity tag. When the reader is farther than the close proximity distance or the detectable range from the tag, the tag reader is unable to read or capture information on the close proximity tag. In an example, the detectable range is less than 10 centimeters (cm). In another example, the detectable range is less than 1 m. In another example, the detectable range is less than 10 m. The close proximity tag can be placed in a convenient location in a room (e.g., an x-ray room). The close proximity tag may be included in a label with adhesive allowing the tag to be attached to the convenient location. Often the tag reader gets so close to the close proximity tag that it appears that the tag reader or the device (e.g., imaging device) housing of the tag reader is tapping the close proximity tag. Thus, "tapping" a tag refers to putting a device that includes the tag reader in close proximity (e.g., the detectable range) to the close proximity tag. In an example, the close proximity tag is an unpowered tag that does not include a power source to power the tag. The automatic identification and data capture (AIDC) technology includes the close proximity tag, tag reader, and tag programmer. AIDC includes the devices, systems, and methods of automatically identifying objects, collecting data about them, and entering that data directly into computer systems (e.g., without human involvement in the data entry). The close proximity tag can include a near field communication (NFC) tag that can be read by a NFC reader, a radio-frequency identification (RFID) microchip that can be read by a RFID reader, a scannable image that includes information that can be read by an optical reader, a barcode that can be read by a barcode reader, or a magnetic stripe that can be read by a magnetic reading head.

NFC is a set of close-range wireless communication protocols for very short-range radio transmissions. NFC enable two electronic devices (e.g., a portable device or a tag) to establish communication by bringing them within a detectable range (i.e., close proximity) of each other, such as 10 cm (approximately 4 inches [in]). NFC employs electromagnetic induction between two loop antenna when NFC devices (e.g., a NFC reader and a NFC tag) exchange information. NFC can operate within a globally available unlicensed radio frequency ISM band of approximately 13.56 megahertz (MHz) on an International Organization for Standardization (ISO) and the International Electrotechnical Commission (IEC) (ISO/IEC) 18000-3 air interface at rates ranging from 106 to 424 kilobits per second (kbit/s). NFC devices (e.g., NFC reader) can work in at least three modes: NFC card emulation, NFC reader/writer, and NFC peer-to-peer. NFC card emulation mode enables NFC-enabled devices, such as smartphones, to act like smart cards, which allows users to perform transactions such as payment or ticketing. NFC reader/writer mode enables NFC-enabled devices to read information stored on inexpensive NFC tags embedded in labels or smart posters. NFC peer-to-peer mode enables two NFC-enabled devices to communicate with each other to exchange information in an adhoc fashion.

In the NFC reader/writer mode, the WAP configuration data can be programmed or written onto the NFC tag. Programming of the NFC tag can be performed by a device, such as a smart phone, that includes a NFC writer and a NFC programming application. The NFC tag can be read by a NFC reader. An NFC module may integrate the NFC reader and NFC writer functions. An NFC tag is a passive device, which operates without its own power supply and is reliant on an active device (e.g., NFC reader or NFC writer) to come into range before the NFC tag is activated. In order to power these NFC tags, electromagnetic induction in coils of wire in the NFC tag is used to create a current in the passive device and the current is used to power circuitry in a microchip. The NFC tag can include an induction coil and a tiny microchip (e.g., non-volatile random-access memory [NVRAM] or flash memory) that can electrically store and recall information.

RFID is a wireless use of electromagnetic fields to transfer data, which can be used for automatically identifying and tracking tags attached to objects. The RFID tag or microchip can include electronically stored information. Some tags can be powered by electromagnetic induction from magnetic fields produced near the RFID reader. In an example, the RFID tag includes an induction coil and a microchip. While NFC and RFID technologies have some similarities, RFID waves can have longer ranges (e.g., up to 100 m) than the NFC range (e.g., up to 20 cm) and the RFID tags may be larger, bulker, and more expensive than NFC tags (i.e., NFC tags may be smaller, thinner, and cheaper than the RFID tags). The RFID reader may consume more power than the NFC reader to induce sufficient current in the induction coils of the tag. In some examples, NFC technology allows two-way communication, while RFID may only provide one-way reading or programming technology. In a configuration, NFC technology is an extension of RFID technology.

Barcodes or scannable images can also include information (e.g., the WAP configuration data). A barcodes is an optical machine-readable representation of data relating to the object to which the barcode is attached (e.g., workstation or WAP). Barcodes can be a linear or one-dimensional (1D) type barcode or rectangles, dots, hexagons and other geometric patterns in a matrix or two-dimensional (2D) type barcode. Examples of the linear barcode include European Article Numbers (EAN) and the Universal Product Code (UPC). Examples of the matrix barcode include Quick Response code (QR code), Aztec Code, Portable Data File 417 (PDF417), MaxiCode, Data Matrix, CrontoSign, and ShotCode. Barcodes can be printed on labels or tags (e.g., paper) using a barcode printer. A barcode reader (or barcode scanner) is an electronic device that can read and output printed barcodes to a computer. Conventionally, the barcode reader includes a light source (e.g., laser), a lens, and a light sensor translating optical impulses from the barcode into an electrical signal or digital code. Although barcodes are specifically discussed, any scannable image that contains information, such as the WAP configuration data, and can be read by an optical scanner can be used.

The controller 240 is a circuit that interfaces with various modules (e.g., wireless LAN transceiver 220 and tag reader 230) of the imaging device and other peripheral devices and can manage the operation of the imaging device. The processor can include a microprocessor, a field-programmable gate array (FPGA), or a state machine. The microprocessor is a computer processor that incorporates the functions of a central processing unit (CPU) with instruction code on a single IC. The FPGA is an integrated circuit (IC) designed to be configured by a customer or a designer after manufacturing. The state machine corresponds to a mathematical model of computation used to design sequential logic circuits, which uses one of a finite number of states in operation. In an example, the controller 240 is integrated with imaging matrix 210, the wireless LAN transceiver 220, or tag reader 230. In another example, the controller function is provided by a combination of the imaging matrix, the wireless LAN transceiver, and tag reader.

In a configuration, the imaging device 200 includes an indicator 250 that alerts or notifies a user that the WLAN transceiver has been configured with the WAP configuration data. The indicator can be coupled to the controller 240, the tag reader 230, or the wireless LAN transceiver 220. Because the wireless LAN transceiver is automatically configured with the WAP configuration data using the close proximity tag, a user may not know if the wireless LAN transceiver is configured with the new WAP configuration data (e.g., that the tag reader was close enough to read the tag) or still has the old WAP configuration data prior to capturing imaging data. In an example, the workstation can display an indication or imaging device identifier (ID) showing that the imaging device is configured to communicate with the workstation, such as a pop up window or blinking screen. Alternatively, the imaging device includes an indicator, such as a speaker, a light, a light emitting diode (LED), or a display (e.g., liquid crystal display [LCD], organic light-emitting diode [OLED] display, or active-matrix OLED [AMOLED] display). For example, when the wireless LAN transceiver is configured with the new WAP configuration data, a speaker may produce a specified sound, a specified color LED illuminates, a specified sequence of LEDs illuminates, or a display displays the configured WAP or some other status or indicator indicating that the wireless LAN transceiver is configured with the new WAP configuration data.

In another example, the speaker may produce a different sound if the tag reader attempts to read a close proximity tag and is unable to extract the WAP configuration data or is unable to configure the wireless LAN transceiver with the new WAP configuration data. Alternatively or additionally, the LED may illuminate a different color or other visual indicator if the tag reader attempts to read a close proximity tag and is unable to extract the WAP configuration data or is unable to configure the wireless LAN transceiver with the new WAP configuration data. The indicator can provide a quick notification to a user of the status of the wireless LAN transceiver's configuration.

In another example, the imaging device 200 includes energy storage 260 that provides electrical power to the components and circuitry of the imaging device. The energy storage device can include a battery (e.g., rechargeable battery) or capacitor (e.g., super capacitor). The energy storage device can be charged via a cable, docketing station or contacts, or via electromagnetic induction.

In another example (not shown), the imaging device 200 can include a motion sensor and a timer. The operations of tag reader (e.g., reading or scanning) can be rare or infrequent relative to capturing images using the imaging matrix or transmitting image date via the wireless LAN transceiver. As a result, a tag reader may consume unnecessary energy (e.g., drain on the battery) even when the tag reader is not in use, such as searching for a close proximity tag. Typically, the imaging device is being moved to a close proximity tag when a tag reader is needed to read the WAP configuration data from the tag, so motion of the imaging device can be associated with a tag reader being powered on. A motion sensor, for example, can reduce the energy expenditure of the imaging device by having the tag reader (or other devices or transmitting devices with minimal use) being put into sleep mode after a specified time without movement of the imaging device (as determined by a timer). The motion sensor can include an accelerometer, a gyrometer, a gyroscope, a magnetometer, a barometer, a rotation sensor, or a combination of these sensors. Once the imaging device is moved, the tag reader can be turned on, which allows the tag reader to read or scan the close proximity tag. The timer can then be used to turn off the tag reader after the specified time (e.g., 30 seconds) without movement. Alternatively, the tag reader may also be powered on and off with separate power switch (e.g., on/off switch) on the housing of the imaging device when the tag reader is not in use or not needed, or the tag reader can be powered on and off with a power switch also used for the imaging device.

The imaging device 200 (or panel) illustrated in FIG. 4 can eliminate the need for a network service or a cable to configure the imaging device for sharing, thus making the act of sharing imaging devices (e.g., wireless portable detectors) relatively easy. The imaging device can remove the need for user interaction with the workstation directly in configuring the wireless LAN transceiver and reduce the errors associated with human data entry.

Figure 5:
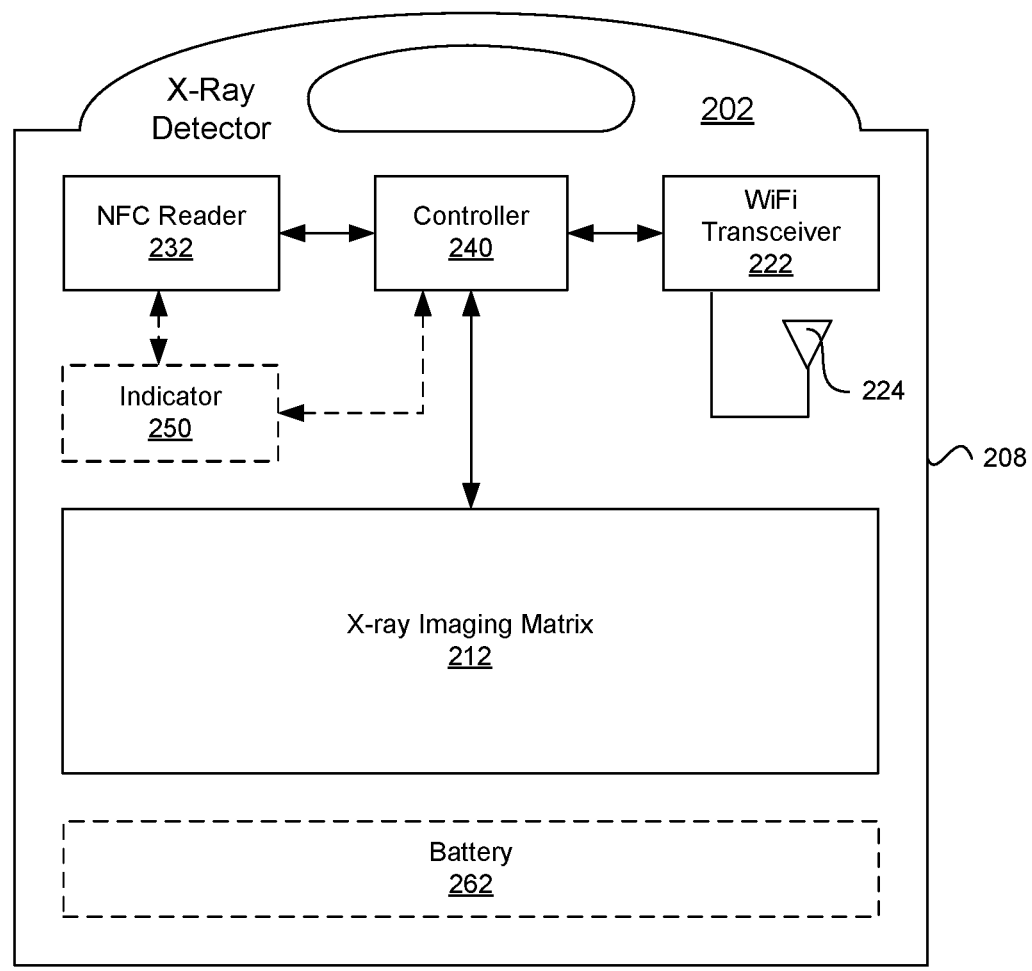
FIG. 5 illustrates a block diagram of an example x-ray detector with a near field communication (NFC) reader.

FIG. 5 illustrates an imaging device or x-ray detector 202 (or x-ray panel), which can be used for medical imaging. X-ray detector 202 includes a housing 208, an x-ray imaging matrix 212 of x-ray pixel detector elements, a WiFi transceiver 222 that allows wireless communication with a WAP, a NFC reader 232 that reads a NFC tag, and a controller 240 that controls the x-ray detector or coordinates communication between x-ray detector modules (e.g., WiFi transceiver and NFC reader). In a configuration, the x-ray imaging matrix 212 (FIG. 2) includes a scintillator layer. The WiFi transceiver 222 includes at least one antenna 224. The x-ray detector 202 may also include an indicator 250 or a battery 262.

Figure 6A:
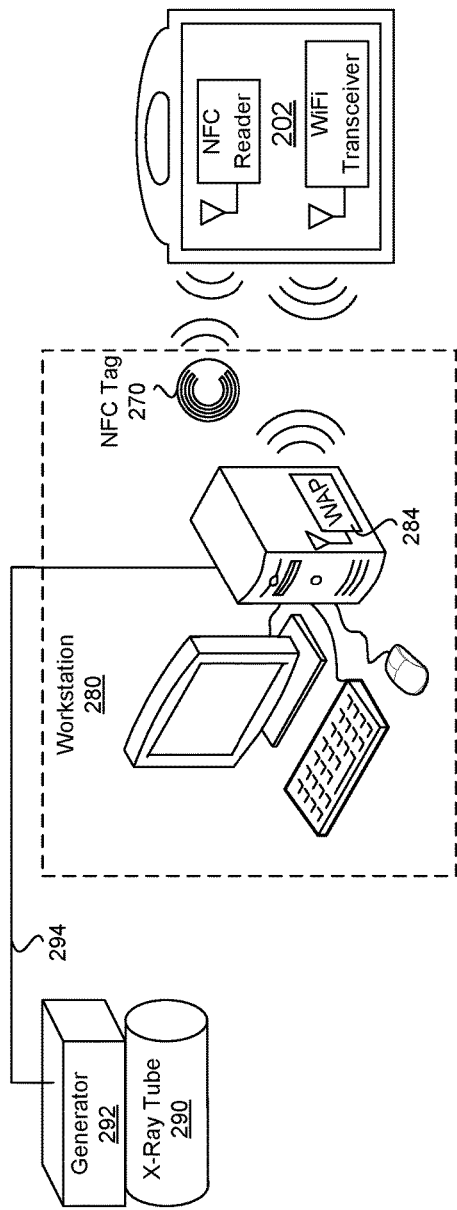
FIG. 6A illustrates a block diagram of an example x-ray system that includes an x-ray detector communicating with a workstation via a wireless access point (WAP) and the workstation includes an NFC tag and has a wired or optical connection to the x-ray tube.
Figure 6B:
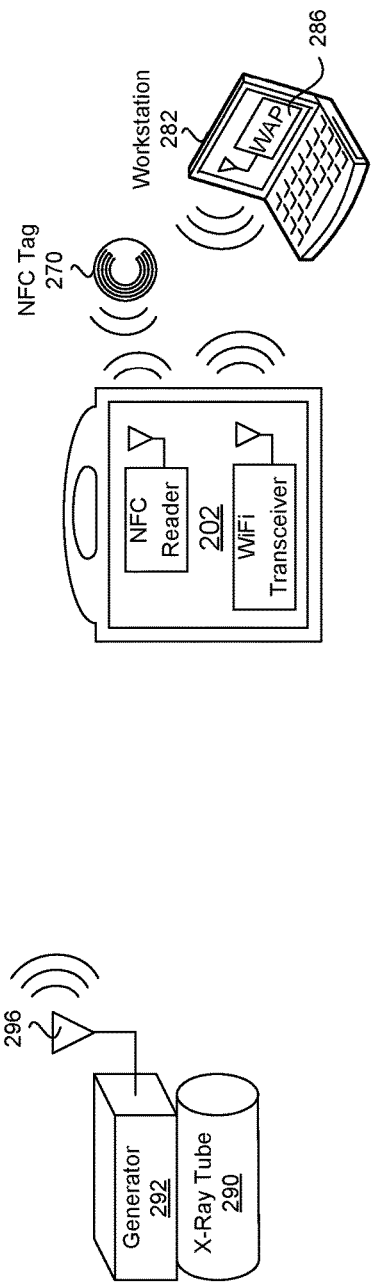
FIG. 6B illustrates a block diagram of an example x-ray system that includes an x-ray detector communicating with a workstation via a WAP and the workstation includes an NFC tag and has a wireless connection to the x-ray tube.

FIGS. 6A and 6B illustrate the x-ray detector 202 scanning an NFC tag 270 associated with a workstation 280 or 282, which can be used to configure a WiFi transceiver (222 in FIG. 5) of the x-ray detector with the WAP 284 or 286 of the workstation. In an example, the NFC tag is located within 10 m of the workstation. Once the WiFi transceiver is configured with the WAP configuration data, the WiFi transceiver can communicate with the workstation, a tube generator 292, or a x-ray tube 290 via the WAP. The WAP 284 or 286 may include a single antenna or multiple antennas. The WAP 286 may be integrated into the workstation 282 or the WAP 284 may be integrated into a component of the workstation 280. The workstation 282 may be a single integrated system (e.g., laptop), or the workstation 280 may have various components and peripheral devices. The workstation 280 or 282 can include a input device (e.g., keyboard, mouse, USB port, disk drive, or transceiver), an output device (e.g., display or monitor, USB port, disk drive, or transceiver), at least one processor or controller, or memory. The workstation 280 or 282 can be used to control the operations and functionality of the tube generator 292, the x-ray tube 290, or the x-ray detector 202. The workstation 280 or 282 can also be used to capture and collect image data. FIG. 6A shows a wired or optical link or connection between the workstation 280 and the tube generator and the x-ray tube. FIG. 6B shows a wireless link between the workstation 282, the tube generator and the x-ray tube, and the x-ray detector 202. The tube generator 292 or the x-ray tube 290 may include a wireless LAN transceiver (e.g., WiFi transceiver) with at least one antenna 296. The x-ray detector 202 may communicate to the tube generator and the x-ray tube directly or via the workstation 282.

Figure 7:
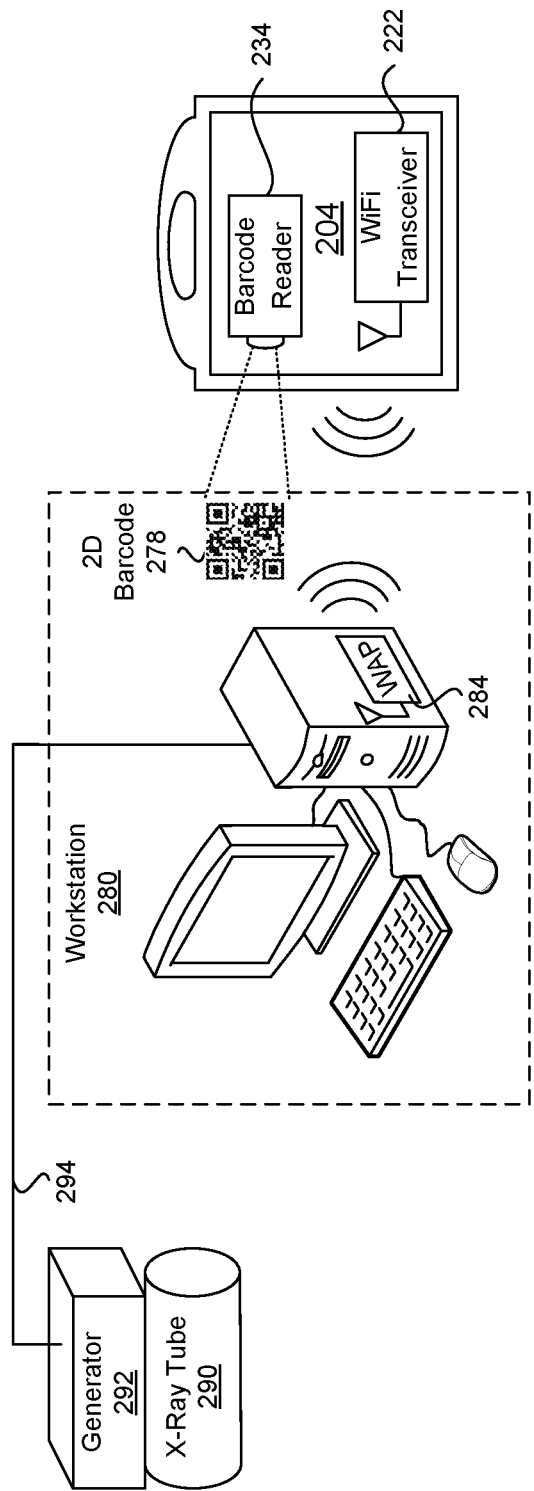
FIG. 7 illustrates a block diagram of an example x-ray system that includes an x-ray detector communicating with a workstation that includes a barcode via a WAP.

FIG. 7 illustrates the x-ray detector 204 with a barcode reader 234, as the tag reader, scanning a QR code (i.e., 2D barcode 278), as the close proximity tag, which is associated with the workstation 280. The barcode reader and barcode can be used to configure a WiFi transceiver 222 of the x-ray detector with the WAP 284 of the workstation. As shown, various technologies can be used for the tag reader, the close proximity tag, and the wireless LAN transceiver.

Figure 8:
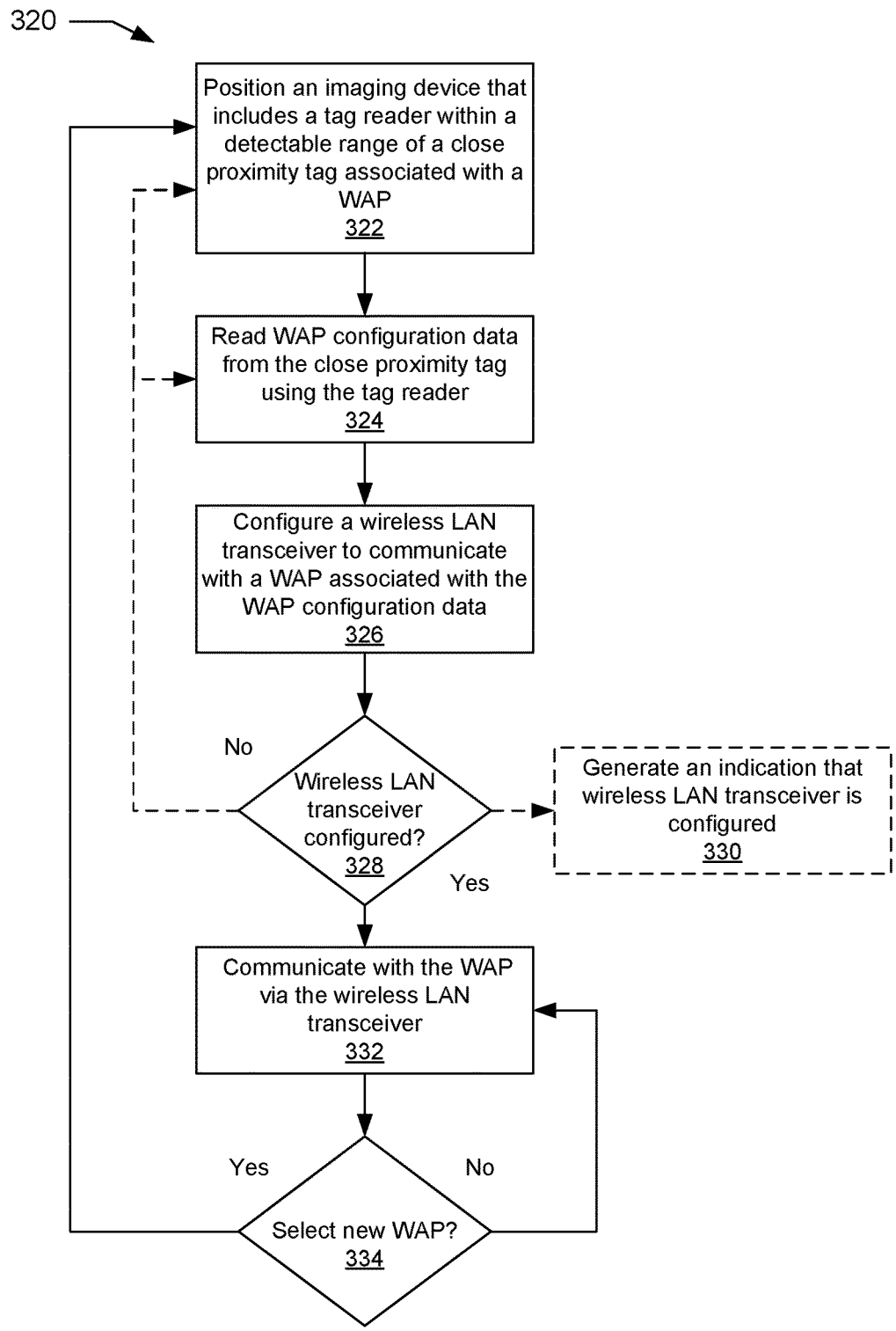
FIG. 8 illustrates a flowchart for configuring an imaging device for communication with a WAP using a close proximity tag.

FIG. 8 illustrates a flowchart 320 for configuring an imaging device for communication with a WAP using a close proximity tag. The imaging device that includes a tag reader can be positioned a detectable range of a close proximity tag associated with a WAP 322. Next, the tag reader can read the WAP configuration data from the close proximity tag 324. Then the wireless LAN transceiver can be configured to communicate with a WAP associated with the WAP configuration data 326. In an example, the imaging device may reboot as part of the reconfiguration of the wireless LAN transceiver. Next, the user or imaging device can verify that the wireless LAN transceiver is reconfigured with the new WAP configuration data 328. If the wireless LAN transceiver is not reconfigured with the new WAP configuration data, the imaging device can generate an indication (e.g., audible sound, light emission, or display readout) that the wireless LAN transceiver is not configured with the new data. Alternatively or additionally, the user can reposition the imaging device closer or in a different position to the close proximity tag 322, or the tag reader can rescan or reread the close proximity tag 324 until the wireless LAN transceiver is reconfigured or a timeout error or flag is generated, which may require further diagnostics by a user or technician. If the wireless LAN transceiver is reconfigured with the new WAP configuration data, the imaging device can generate an indication (e.g., sound, light, or display) that the wireless LAN transceiver is configured properly 330. Then the wireless LAN transceiver can communicate with the WAP 332 until a new WAP is selected 334. When a user wants to associate the imaging device with a new WAP (e.g., workstation or x-ray system), the imaging device can be moved to another close proximity tag 322 and the process repeats.

Figure 9:
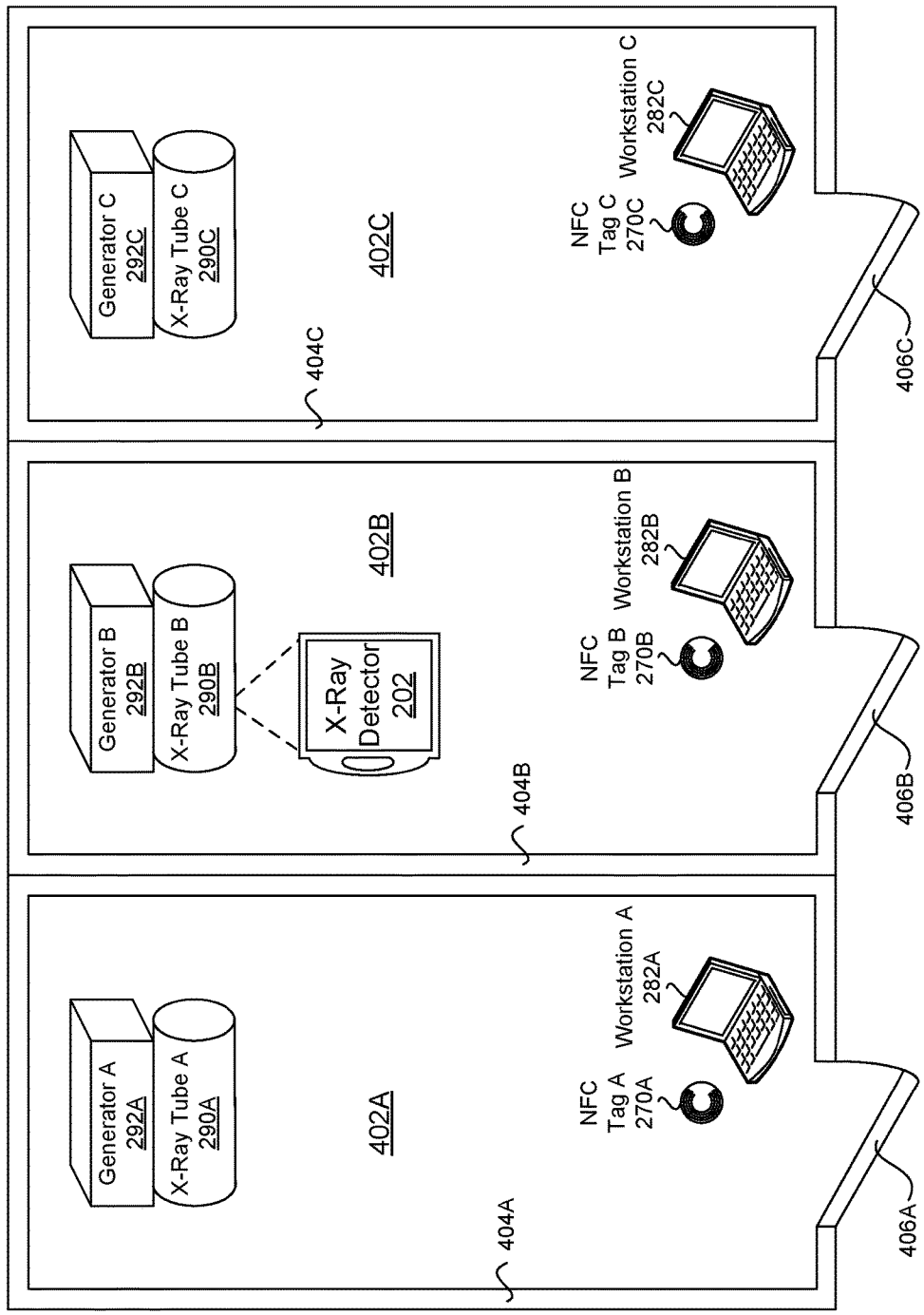
FIG. 9 illustrates a block diagram of an example x-ray detector that can be configured to multiple workstations where each workstation is associated with a WAP.

FIG. 9 illustrates an implementation of the configuration of workstations 282A-C and WAPs using NFC tags 270A-C. The diagram shown in FIG. 9 illustrates three x-ray rooms 402A-C where each x-ray room includes a x-ray tube 290A-C, a tube generator 292A-C, and a workstation 282A-C. The x-ray detector 202 may be used with any of the x-ray systems (e.g., x-ray tubes 290A-C and tube generators 292A-C) in the x-ray rooms. Each x-ray room may include walls 404A-C and a door 406A-C that are lined with a shielding material (e.g., lead) that blocks electromagnetic radiation, such as x-rays and RF signals, so the WAP for each x-ray system may be located within the room. Each NFC tag 270A-C includes the WAP configuration data for the WAP associated with the workstation 282A-C.

Figure 10:
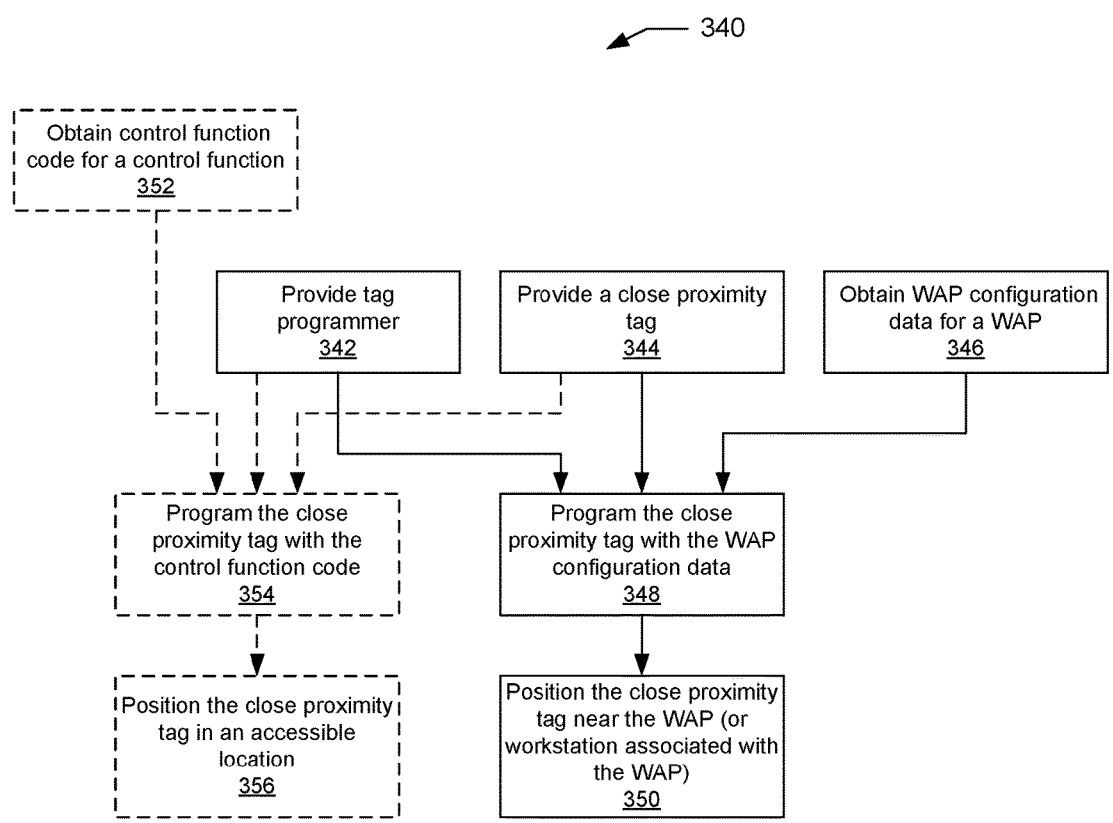
FIG. 10 illustrates a flowchart for programming a close proximity tag with WAP configuration data.

The close proximity tags 344 can be programmed with a tag programmer 342 (e.g., NFC writer) or a tag printer (e.g., barcode printer), as illustrated in FIG. 10. With the WAP configuration data for a WAP 346, the tag programmer 342 can program the close proximity tag with the WAP configuration data 348. Then, the close proximity tag can be placed near the WAP (or a convenient or conspicuous place near the workstation associated with the WAP) 350.

The close proximity tags 344 can also be used to quickly perform a control function, such as resetting the image device to default settings (or factory settings) or changing a setting or group of settings on the image device. A user can obtain a control function code (e.g,. COMMAND=reset-to-factory-default-settings) for a control function 352. The tag programmer 342 can program the close proximity tag with the control function code 354. Then, the close proximity tag can be placed in an accessible location 356.

Figure 11:
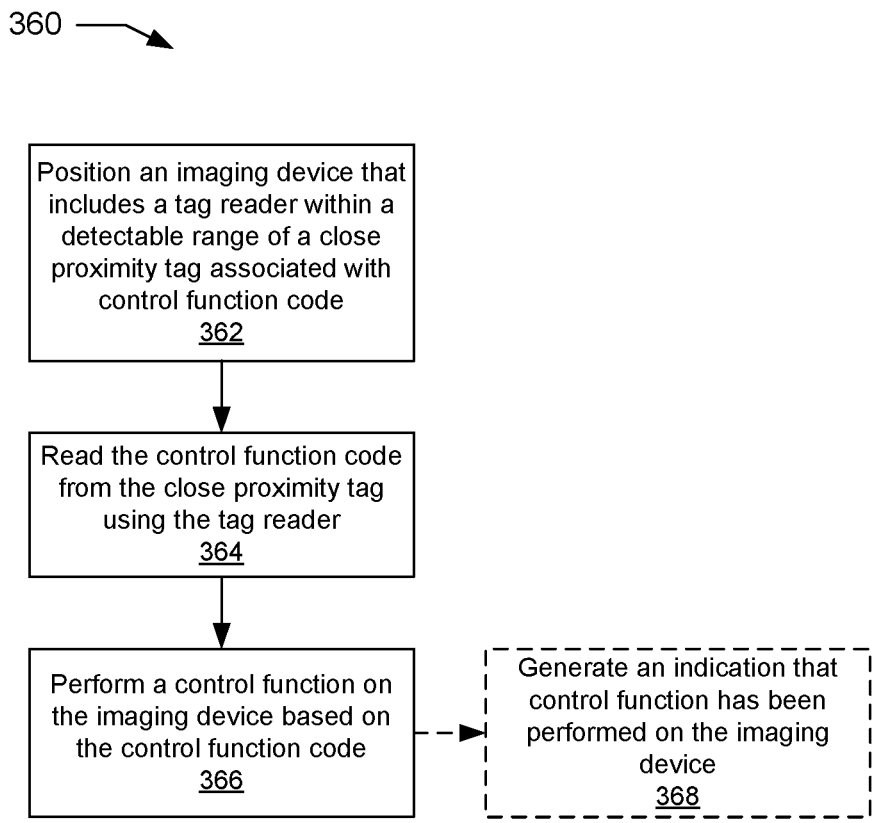
FIG. 11 illustrates a flowchart for performing a control function on an imaging device using a close proximity tag.

FIG. 11 illustrates a flowchart for performing a control function on an imaging device using a close proximity tag. The imaging device, which includes the tag reader, is positioned or placed within a detectable range of a close proximity tag associated with the control function 362. The tag reader reads the control function code from the close proximity tag 364. Then, the imaging device performs the control function based on the control function code 366. In an example, the control function resets the imaging device to default settings (e.g., factory settings), changes a setting of the image device, or provides another command that can be performed by the imaging device. In an example, the imaging device generates an indication (e.g., sound, light, or display e.g., RESET or DEFAULT]) that the control function has been performed on the imaging device 368.

Figure 12:
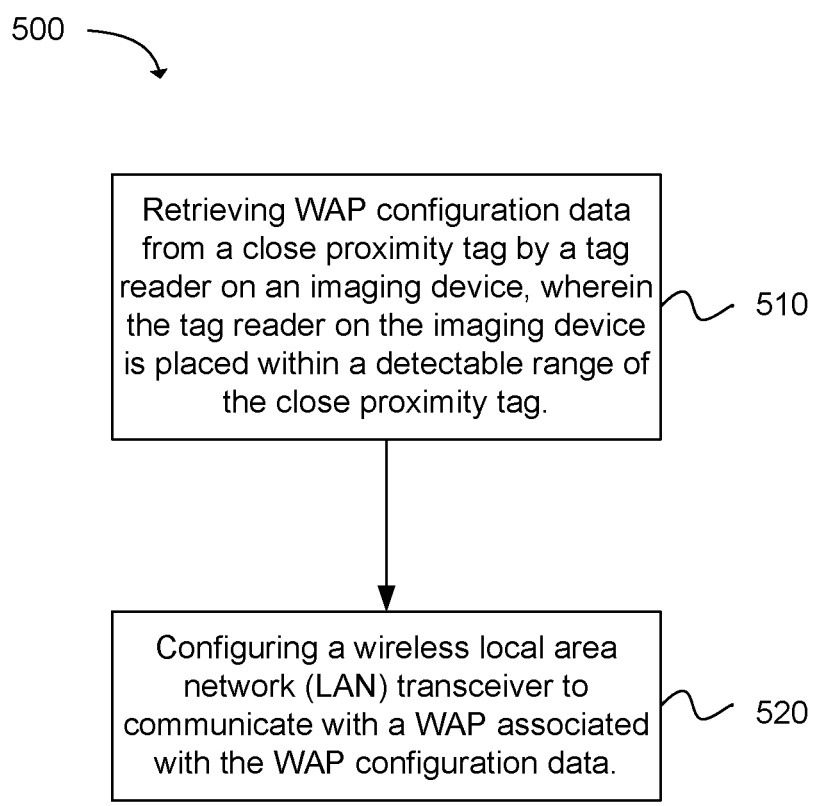
FIG. 12 is flowchart illustrating an example of a method of configuring an imaging device for communication with a WAP using a close proximity tag.

The flowchart shown in FIG. 12 illustrates a method 500 of configuring an imaging device for communication with a WAP using a close proximity tag. The method may be executed as instructions on a machine or computer circuitry, where the instructions are included on at least one computer readable medium or at least one non-transitory machine readable storage medium. The method includes the step of retrieving WAP configuration data from a close proximity tag by a tag reader on an imaging device, wherein the tag reader on the imaging device is placed within a detectable range of the close proximity tag, as in step 510. The next step of the method includes configuring a wireless LAN transceiver to communicate with a WAP associated with the WAP configuration data, as in step 520.

Figure 13:
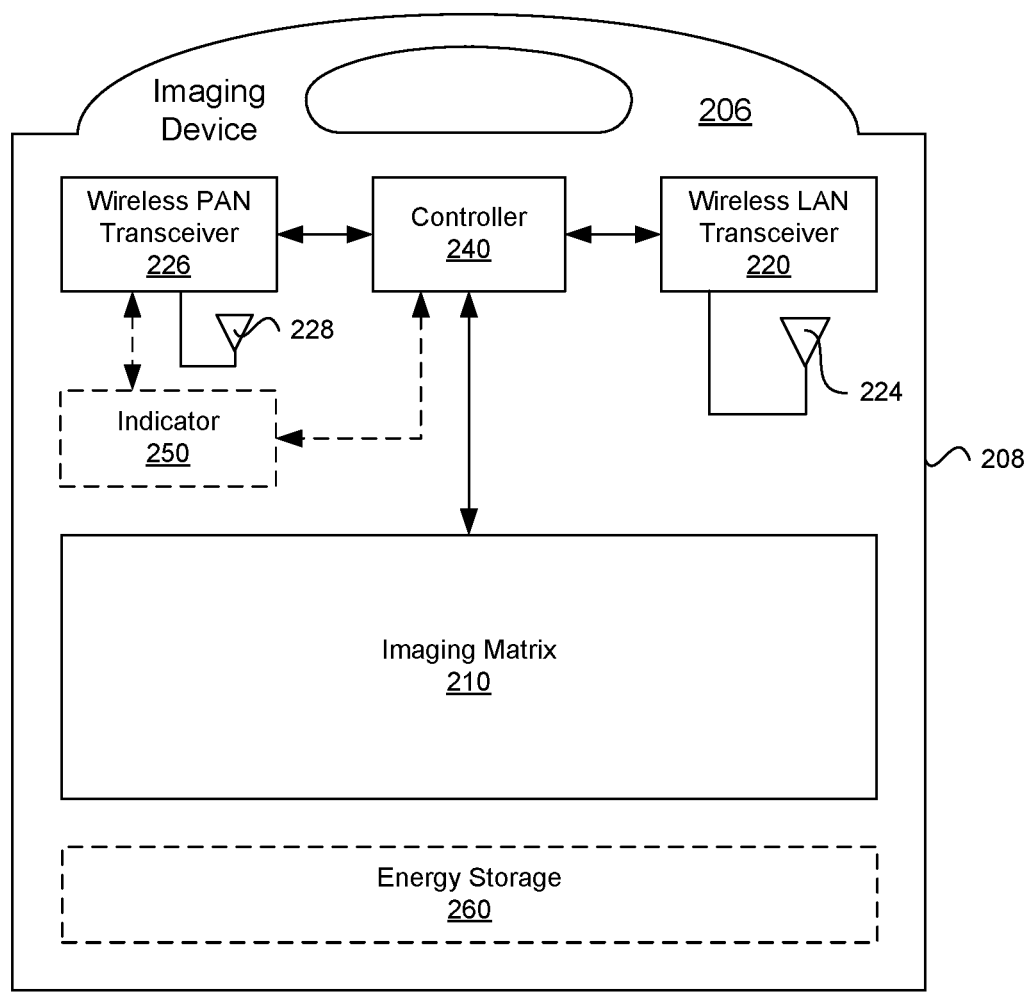
FIG. 13 illustrates a block diagram of an example imaging device with a wireless personal area networks (PAN) transceiver and a wireless local area network (LAN) transceiver.

FIG. 13 illustrates an imaging device 206 that can configure the wireless LAN transceiver 220 (e.g., configured for WiFi) for wireless communication with a WAP using a wireless PAN transceiver 226 (e.g., configured for Bluetooth). The imaging device 206 includes a housing 208, an imaging matrix 210 of pixel detector elements, a wireless LAN transceiver 220 that allows wireless communication with the WAP, a wireless PAN transceiver 226 that that allows wireless communication with a PAN WAP (not shown) or a corresponding wireless PAN (not shown; e.g., in a workstation), and a controller 240 that controls the imaging device or coordinates communication between imaging device modules (e.g., wireless LAN transceiver and wireless PAN transceiver). The wireless PAN transceiver 226 includes at least one antenna 228. The imaging device 206 may also include an indicator 250 or energy storage 260.

A wireless PAN transceiver 226 can have a short effective transmission range (e.g., less than 10 m) similar to a tag reader. Thus, the wireless PAN transceiver may perform a similar function to a tag reader as previously discussed. The wireless PAN transceiver of the imaging device can be paired with the corresponding wireless PAN or the PAN WAP associated with each workstation or WAP (e.g., in each room). Pairing is a process that allows two devices (e.g., wireless PAN transceivers) to establish a communication link. Conventionally, the pairing process is triggered by either device making specific request to establish a link and a relationship is established by creating a shared secret known as a link key. A user may be involved in providing a pairing response or acknowledgment. In an example, the distance between workstations or electromagnetic shielding between workstations (e.g., x-ray rooms) may only allow one corresponding wireless PAN or one PAN WAP to communicate with the wireless PAN transceiver of the imaging device at a time. Instead of using the close proximity tag to store the WAP configuration data, the WAP configuration data (i.e., LAN WAP configuration data) may be stored in a component (e.g., memory) of the workstation. Each time the wireless PAN transceiver (of the imaging device) gets within transmission range of a corresponding wireless PAN or a PAN WAP associated (with a workstation), the corresponding wireless PAN or the PAN WAP can send the LAN WAP configuration data to the wireless PAN transceiver. Then, the imaging device 206 can configured the wireless LAN transceiver 220 for wireless communication with the WAP associated with the workstation. When the wireless PAN transceiver gets within transmission range of another corresponding wireless PAN or another PAN WAP associated with another workstation, the imaging device configures the wireless LAN transceiver for wireless communication with the WAP associated with the other workstation.

The technology (devices, systems, and methods) described herein can provide an efficient mechanism for configuring a wireless LAN transceiver of an imagining device for wireless communication with a WAP without a physical connection (e.g., wired or optical) to the workstation using a cable and without running a specific configuration application or program. Eliminating the cable for configuring the wireless LAN transceiver can reduce or eliminate the issues associated with cables, such as the length of the cable limiting the range or the position that the imaging device can be used, the cable can get lost or misplaced, the cable can cause a tripping hazard, or the cable or cable connectors can get damaged to repeatability of use. In some examples, the configuration of the wireless LAN transceiver does not require WAP configuration information or data to be previously stored in the workstation. The configuration of the wireless LAN transceiver as described provides an easier process for a user and results in a much better user experience. In some examples (e.g., NFC tag and NFC reader), using the close proximity tag reduces the range in which an imaging device may accidentally come within range of the close proximity tag, which can reduces unwanted accidental reconfigurations.

Circuitry can include hardware, firmware, program code, executable code, computer instructions, and/or software. A non-transitory computer readable storage medium can be a computer readable storage medium that does not include a signal.

It should be understood that many of the functional units described in this specification have been labeled as modules, in order to more particularly emphasize their implementation independence. For example, a module may be implemented as a hardware circuit comprising custom very-large-scale integration (VLSI) circuits or gate arrays, including but not limited to logic chips, transistors, or other components. A module may also be implemented in programmable hardware devices, including but not limited to field programmable gate arrays (FPGA), programmable array logic, programmable logic devices or similar devices.

Reference throughout this specification to an "example" or an "embodiment" means that a particular feature, structure, or characteristic described in connection with the example is included in at least one embodiment of the invention. Thus, appearances of the words an "example" or an "embodiment" in various places throughout this specification are not necessarily all referring to the same embodiment.

Furthermore, the described features, structures, or characteristics may be combined in a suitable manner in one or more embodiments. In the following description, numerous specific details are provided (e.g., examples of layouts and designs) to provide a thorough understanding of embodiments of the invention. One skilled in the relevant art will recognize, however, that the invention can be practiced without one or more of the specific details, or with other methods, components, layouts, etc. In other instances, well-known structures, components, or operations are not shown or described in detail to avoid obscuring aspects of the invention.

While the forgoing examples are illustrative of the principles of the invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited. Various features and advantages of the invention are set forth in the following claims.

What is claimed is:

1. A portable imaging device, comprising:
    an imaging matrix of pixel detector elements, wherein each pixel detector element is configured to detect photon energy;
    a tag reader configured to read wireless access point (WAP) configuration data from a close proximity tag and to read a control function code from the close proximity tag or a second close proximity tag, wherein the control function code is selected from a group consisting of an image device setting, a reset to default settings command, and combinations thereof;
    a controller coupled to the imaging matrix, a wireless local area network (LAN) transceiver, and the tag reader, and configured to initialize the wireless LAN transceiver for communication with a specified WAP using the WAP configuration data and perform a control function on the imaging device based on the control function code; and
    the wireless local area network (LAN) transceiver configured to transmit imaging matrix data to the specified WAP after the control function is performed on the imaging device.

2. The imaging device of claim 1, wherein the tag reader is selected from a group consisting of a near field communication (NFC) reader, a radio-frequency identification (RFID) reader, an optical reader, and a barcode reader.

3. The imaging device of claim 1, wherein the WAP configuration data is selected from a group consisting of a service set identifier (SSID), an Internet Protocol address (IP address), a passphrase, a country code, a channel, and combinations thereof.

4. The imaging device of claim 1, further comprising an energy storage component configured to provide power to the imaging device, wherein the energy storage component is selected from a group consisting of a battery and a capacitor.

5. The imaging device of claim 1, further comprising an indicator configured to provide an indication that the specified WAP is configured for communication with the imaging device, wherein the indicator is selected from a group consisting of a speaker, a light, a light emitting diode (LED), a display, and combinations thereof.

6. The imaging device of claim 1, wherein the wireless LAN transceiver is configured to communicate using at least one wireless communication standard selected from a group consisting of WiFi, Institute of Electrical and Electronics Engineers (IEEE) 802.11 standard, Bluetooth, and IEEE 802.15.

7. The imaging device of claim 1, wherein the imaging device is a radiation detector, the imaging matrix is a radiation imaging matrix, and each pixel detector element is a radiation pixel detector element configured to detect radiation.

8. The imaging device of claim 7, wherein the radiation imaging matrix includes a scintillator layer.

9. A method of configuring a portable imaging device for communication with a wireless access point (WAP) using a close proximity tag, the method comprising:
    retrieving WAP configuration data from a first close proximity tag by a tag reader on an imaging device, wherein the tag reader on the imaging device is placed within a detectable range of the first close proximity tag;
    configuring a wireless local area network (LAN) transceiver to communicate with a WAP associated with the WAP configuration data;
    retrieving embedded control function code from one of the first close proximity tag or a second close proximity tag by the tag reader on the imaging device, wherein the tag reader on the imaging device is placed within a detectable range of one of the first close proximity tag or the second close proximity tag, and the embedded control function code is selected from a group consisting of an image device setting, a reset to default settings command, and combinations thereof; and after performing a control function on the imaging device based on the embedded control function code, transmitting data from the imaging device to the WAP.

10. The method of claim 9, further comprising:
communicating with the WAP via the wireless LAN transceiver, wherein the communication includes transmission of image data from the imaging device.

11. The method of claim 10, wherein the imaging device is a radiation detector that is configured to detect radiation and the image data include an image generated from x-rays.

12. The method of claim 10, wherein
communicating with the WAP via the wireless LAN transceiver uses at least one wireless communication standard selected from a group consisting of WiFi, Institute of Electrical and Electronics Engineers (IEEE) 802.11 standard, Bluetooth, and IEEE 802.15; and
the WAP configuration data is selected from a group consisting of a service set identifier (SSID), an Internet Protocol address (IP address), a passphrase, a country code, a channel, and combinations thereof.

13. The method of claim 9, wherein
the tag reader is selected from a group consisting of a near field communication (NFC) reader, a radio-frequency identification (RFID) reader, an optical reader, and a barcode reader; and
the close proximity tag is selected from a group consisting of a NFC tag, a RFID microchip, a scannable image, and a barcode.

14. The method of claim 9, further comprising:
generating an indication when the wireless LAN transceiver is configured to communicate with the WAP, wherein the indication is selected from a group consisting of an audible sound from a speaker, a light emission from a light source, and a readout on a display.

15. The method of claim 9, further comprising:
programming the close proximity tag with the WAP configuration data using a tag programmer, wherein the tag programmer is placed within a detectable range of the close proximity tag; and
positioning the close proximity tag within a communication range of the WAP.

16. The method of claim 9, wherein the detectable range is within one meter.

17. A portable radiation detector, comprising:
a radiation imaging matrix of radiation pixel detector elements, wherein each radiation pixel detector element is configured to detect radiation;
a near field communication (NFC) reader configured to read wireless access point (WAP) configuration data from a NFC tag and to read a control function code from the NFC tag or a second NFC tag, wherein the control function code is selected from a group consisting of a radiation detector setting, a reset to default settings command, and combinations thereof;
a controller coupled to the radiation imaging matrix, the WiFi transceiver, and the NFC reader, and configured to initialize the WiFi transceiver for communication with a specified WAP using the WAP configuration data and perform a control function on the imaging device based on the control function code; and
the WiFi transceiver configured to transmit radiation imaging matrix data to the specified WAP after the control function is performed on the imaging device.

18. The radiation detector of claim 17, wherein the radiation includes x-ray electromagnetic radiation with a wavelength ranging from 0.01 to 10 nanometers (nm).

* * * * *